United States Patent [19]

Yamada

[11] Patent Number: 4,871,676
[45] Date of Patent: Oct. 3, 1989

[54] CELL CULTURE INCUBATOR

[75] Inventor: Koji Yamada, Osaka, Japan

[73] Assignee: Sumitomo Electric Industries, Ltd., Osaka, Japan

[21] Appl. No.: 198,435

[22] Filed: May 25, 1988

[30] Foreign Application Priority Data

May 28, 1987 [JP] Japan .................................. 62-81595
May 28, 1987 [JP] Japan .................................. 62-81596

[51] Int. Cl.$^4$ .......................................... C12M 1/38
[52] U.S. Cl. .................................. 435/290; 435/291; 49/340; 49/345
[58] Field of Search ............... 435/287, 289, 290, 291, 435/292, 285; 422/63, 64, 67; 49/339, 340, 345; 74/99 R

[56] References Cited

U.S. PATENT DOCUMENTS

| | | | |
|---|---|---|---|
| 3,654,091 | 4/1972 | Binnings et al. | 435/291 |
| 3,801,468 | 4/1974 | Lumb et al. | 435/290 |
| 3,886,425 | 5/1975 | Weiss | 49/340 |
| 4,090,921 | 5/1978 | Sawamura et al. | 435/290 |
| 4,250,266 | 2/1981 | Wade | 435/290 |
| 4,584,275 | 4/1986 | Okano et al. | 435/290 |

FOREIGN PATENT DOCUMENTS

| | | | |
|---|---|---|---|
| 2649435 | 12/1977 | Fed. Rep. of Germany | 49/340 |
| 926541 | 5/1963 | United Kingdom . | |
| 1112919 | 5/1968 | United Kingdom . | |

OTHER PUBLICATIONS

European Search Report-EP 88 10 8516-9-20-88.

Primary Examiner—James C. Yeung
Attorney, Agent, or Firm—Cushman, Darby & Cushman

[57] ABSTRACT

An incubator for cell culture used in the field of biotechnology, in which a driving mechanism for rotating a tray stock for supporting a plurality of trays for cell culture is provided outside an incubator housing.

1 Claim, 5 Drawing Sheets

CELL CULTURE INCUBATOR

BACKGROUND OF THE INVENTION

The present invention generally relates to a system for automatically storing in a thermo-hygrostat such as an incubator, trays used for cell culture in the field of biotechnology and more particularly, to improvements to the incubator.

A thermo-hygrostat is proposed in, for example, Japanese Utility Model Laid-Open Publication (unexamined) No. 182300/1986. In this known thermo-hygrostat, a driving mechanism including a motor is provided. Generally, an interior of a thermo-hygrostat is maintained at a high humidity of 90% or more so as to enable cell culture and thus, is a severe environment for the driving mechanism including the motor. Therefore, the motor is required to be accommodated in a casing sealed by a gasket, etc., so that a capacity for accommodating the trays in the thermo-hygrostat is reduced by a space occupied by the casing, etc., thereby resulting in decrease of the number of the trays to be accommodated in the thermo-hygrostat.

Furthermore, due to the above described constructions in which the casing is accommodated in the thermo-hygrostat and the motor, etc. are stored in the casing, the known thermo-hygrostat has such a drawback that if a failure of the motor of the driving mechanism occurs, it is difficult to repair the motor.

Moreover, the known thermo-hygrostat is provided with a door for manually taking the trays out of and into a thermo-hygrostat housing and performing maintenance operation, etc. of the thermo-hygrostat. Hence, the known thermo-hygrostat has been disadvantageous in that in the case where the trays are taken into or out of the thermo-hygrostat housing or maintenance operation of the thermo-hygrostat is performed by opening the door, atmosphere in the thermo-hygrostat housing changes considerably through communication of atmosphere in the thermo-hygrostat housing with ambient air.

SUMMARY OF THE INVENTION

Accordingly, an essential object of the present invention is to provide an incubator in which a driving mechanism is provided outside an incubator housing, with substantial elimination of the disadvantages inherent in conventional incubators of this kind.

Another important object of the present invention is to provide an incubator in which, in addition to a large main door for manually taking trays for cell culture out of and into the incubator housing and performing maintenance operation of the incubator, a small auxiliary door for automatically taking the trays out of and into the incubator housing is provided so as to minimize change of atmosphere in the incubator housing at the time of taking the trays out of and into the incubator housing.

BRIEF DESCRIPTION OF THE DRAWINGS

These objects and features of the present invention will become apparent from the following description taken in conjunction with the preferred embodiments thereof with reference to the accompanying drawings, in which.

Before the description of the present invention proceeds, it is to be noted that like parts are designated by like reference numerals throughout several views of the accompanying drawings.

DETAILED DESCRIPTION OF THE INVENTION

Figure 1:
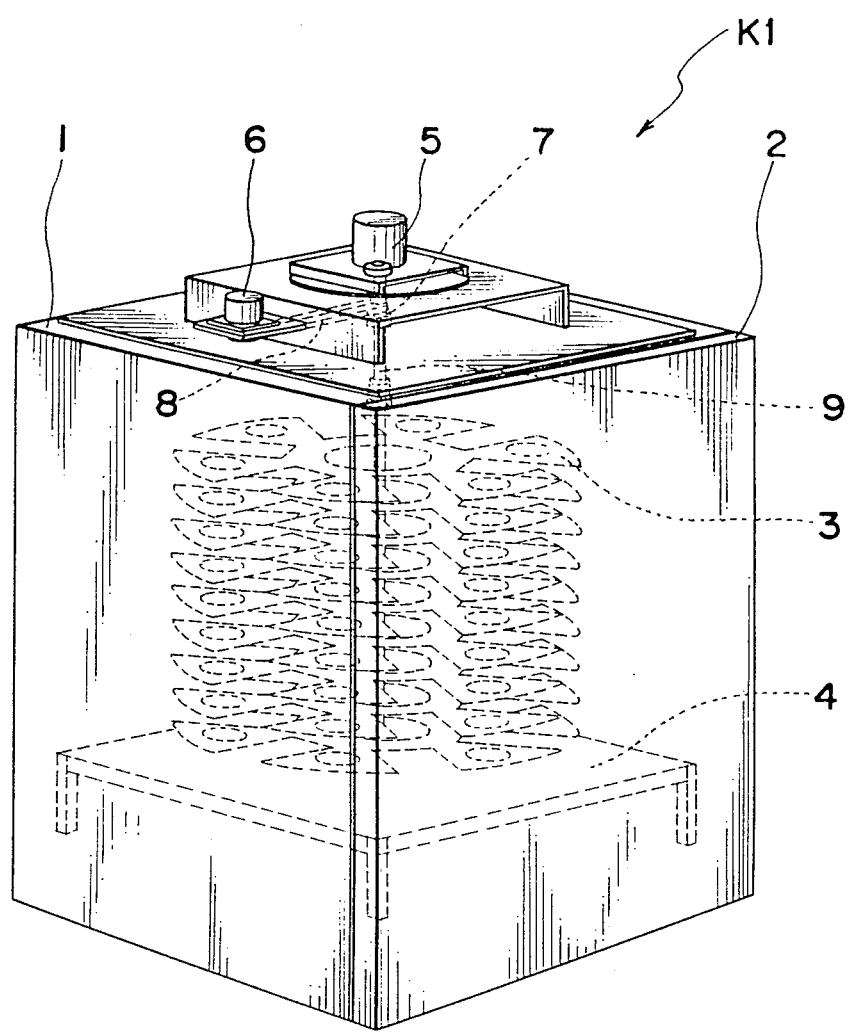
FIG. 1 is a perspective view of an incubator according to a first embodiment of the present invention.
Figure 2:
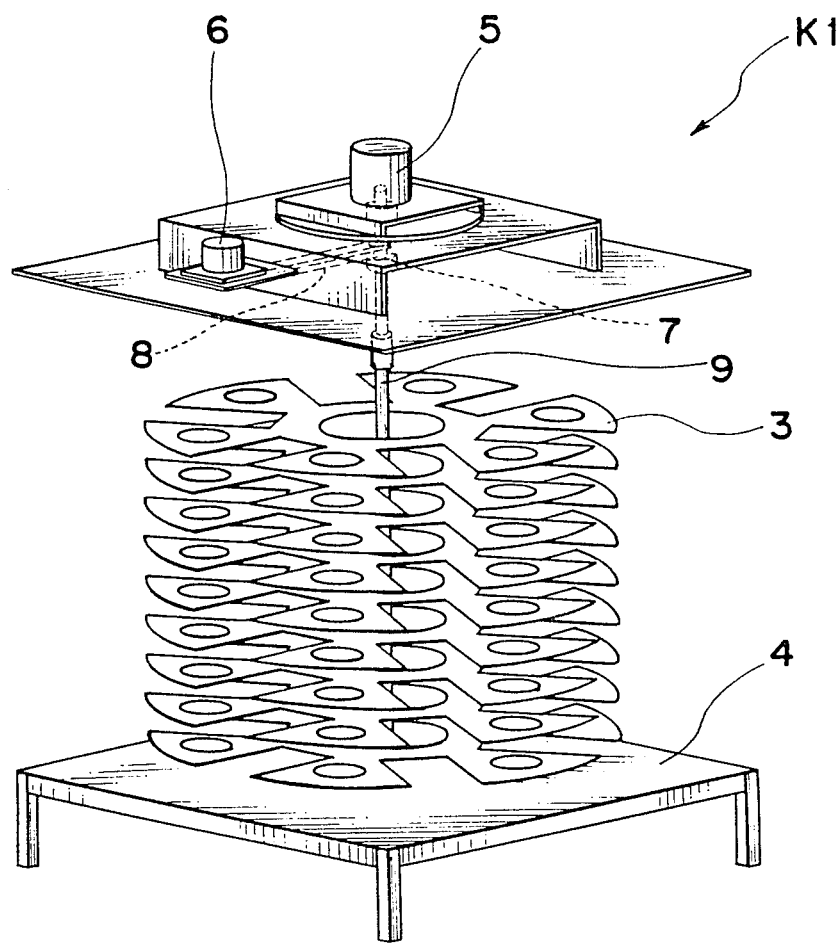
FIG. 2 is a cutaway view of the incubator of FIG. 1.

Referring now to the drawings, there is shown in FIGS. 1 and 2, an incubator K1 according to a first embodiment of the present invention. The incubator K1 includes an incubator housing 1, a main door 2 for manually taking trays for cell culture out of and into the incubator housing 1 and for performing maintenance operation in the incubator housing 1, a tray stock 3 for supporting the trays and a base 4.

The incubator further includes a motor 5, an encoder 6, a coupling 7 and a timing belt 8 which constitute a driving mechanism for driving the tray stock 3 and are disposed outside the incubator housing 1. The tray stock 3 is rotatably supported by thrust bearings, etc. so as to be rotated by the driving mechanism about a vertical shaft 9 mounted on the base 4 such that a desired one of the trays is displaced to a position confronting the main door 2. The shaft 9 extends through a top wall of the incubator housing 1 so as to project upwardly out of the top wall of the incubator housing 1. The shaft 9 is coupled with a motor shaft of the motor by the coupling 7. Rotation of the motor 5 is transmitted to the encoder 6 by the timing belt 8. The motor 5 is disposed at a central portion of the top wall of the incubator housing 1 such that the incubator housing 1 is symmetrical with respect to the motor 5.

In the above described arrangement of the incubator K1, since the driving mechanism is disposed outside the incubator housing 1, a space for the driving mechanism is not required to be provided in the incubator housing 1, thus making the incubator housing 1 compact in size.

Meanwhile, since the driving mechanism is not required to be disposed in the incubator housing 1 held at a high humidity, possibility of failure of the driving mechanism diminishes. Moreover, even if failure of the driving mechanism occurs, it is easy to perform maintenance operation of the driving mechanism disposed outside the incubator. Furthermore, since electric wires for the driving mechanism are not required to be drawn into the incubator housing 1, holes for wiring are not required to be formed on walls of the incubator housing 1, so that the incubator K1 is made simple in structure. In addition, since the motor 5 acting as a source for generating heat is disposed outside the incubator housing 1 and an internal structure of the incubator housing 1 is symmetrical with respect to the rotation axis of the motor 5, temperature distribution in the incubator housing 1 becomes uniform.

As is clear from the foregoing description, in the incubator of the present invention, the driving mechanism is provided outside the incubator housing and the tray stock supported rotatably by the vertical shaft in the incubator housing is driven such that a desired one of the trays is displaced to a position confronting the main door.

Accordingly, in accordance with the present invention, a number of the trays can be accommodated in the incubator housing and maintenance of the incubator can be performed efficiently.

Figure 3:
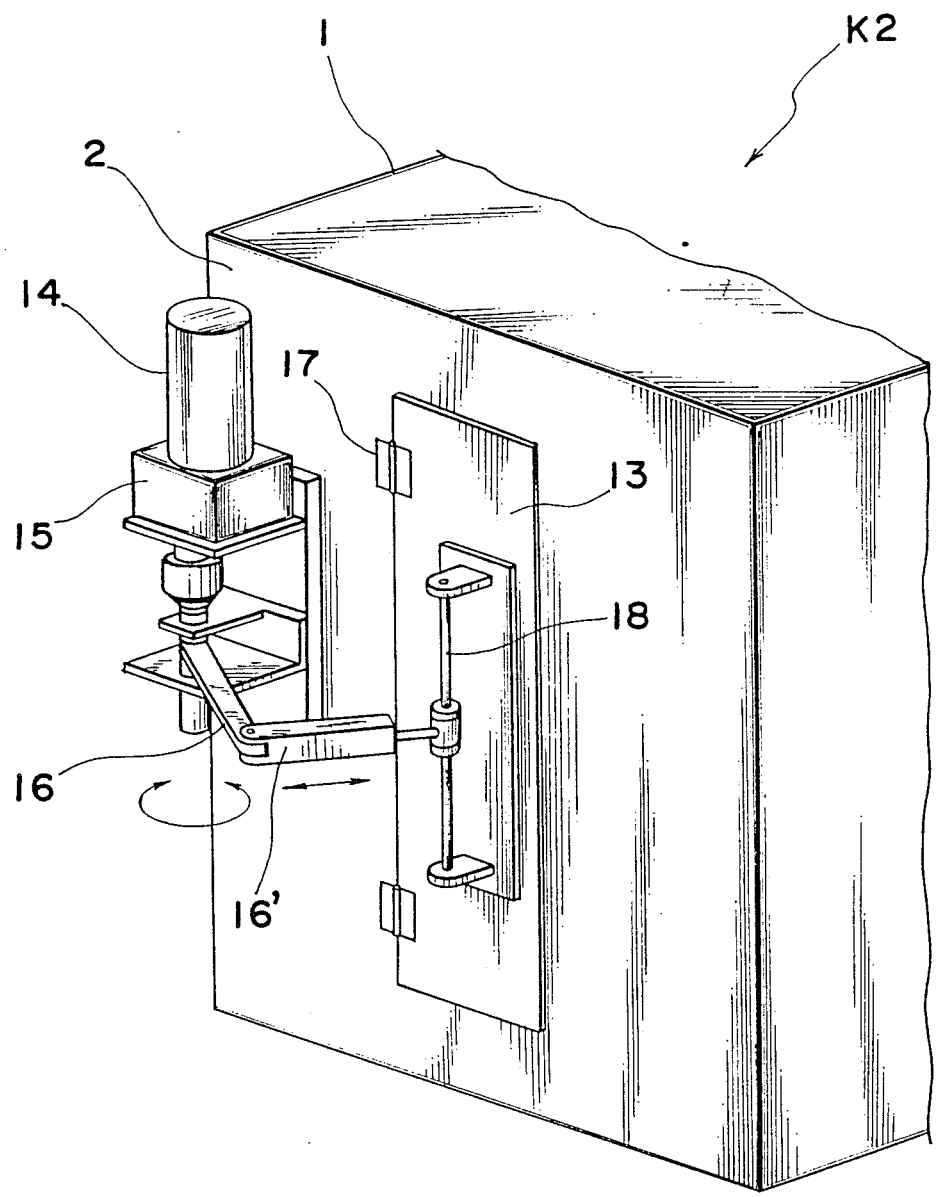
FIG. 3 is a fragmentary perspective view of an incubator according to a second embodiment of the present invention.
Figure 4:
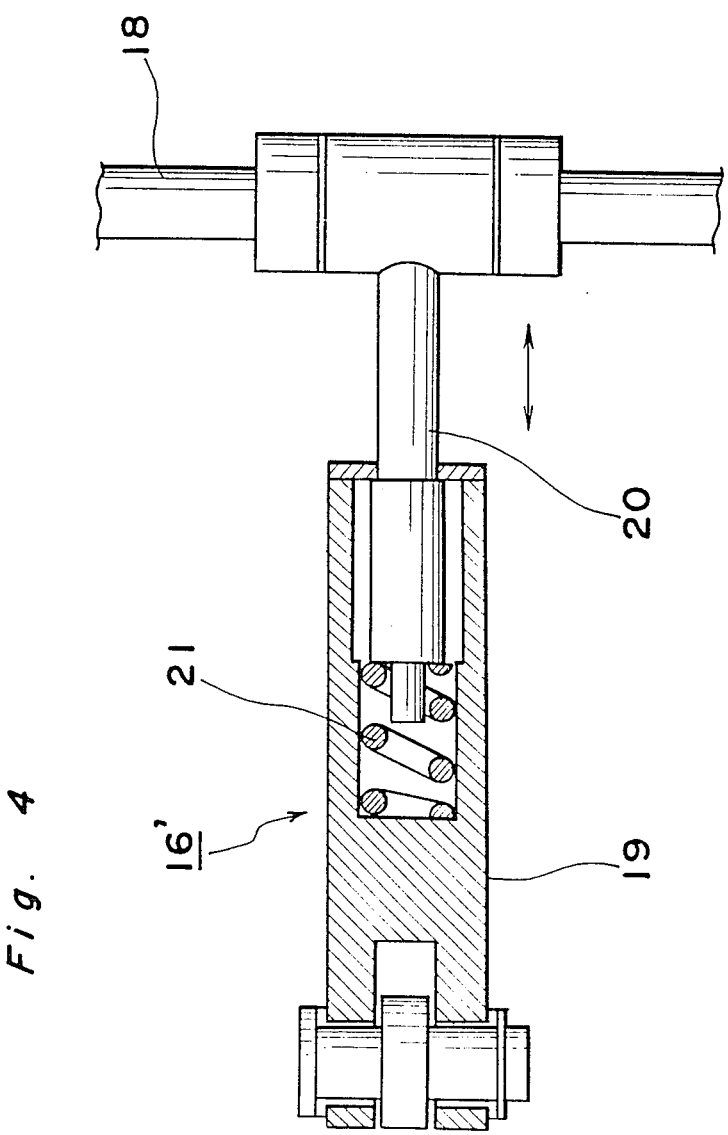
FIG. 4 is a sectional view of a member of a link employed in the incubator of FIG. 3.
Figure 5:
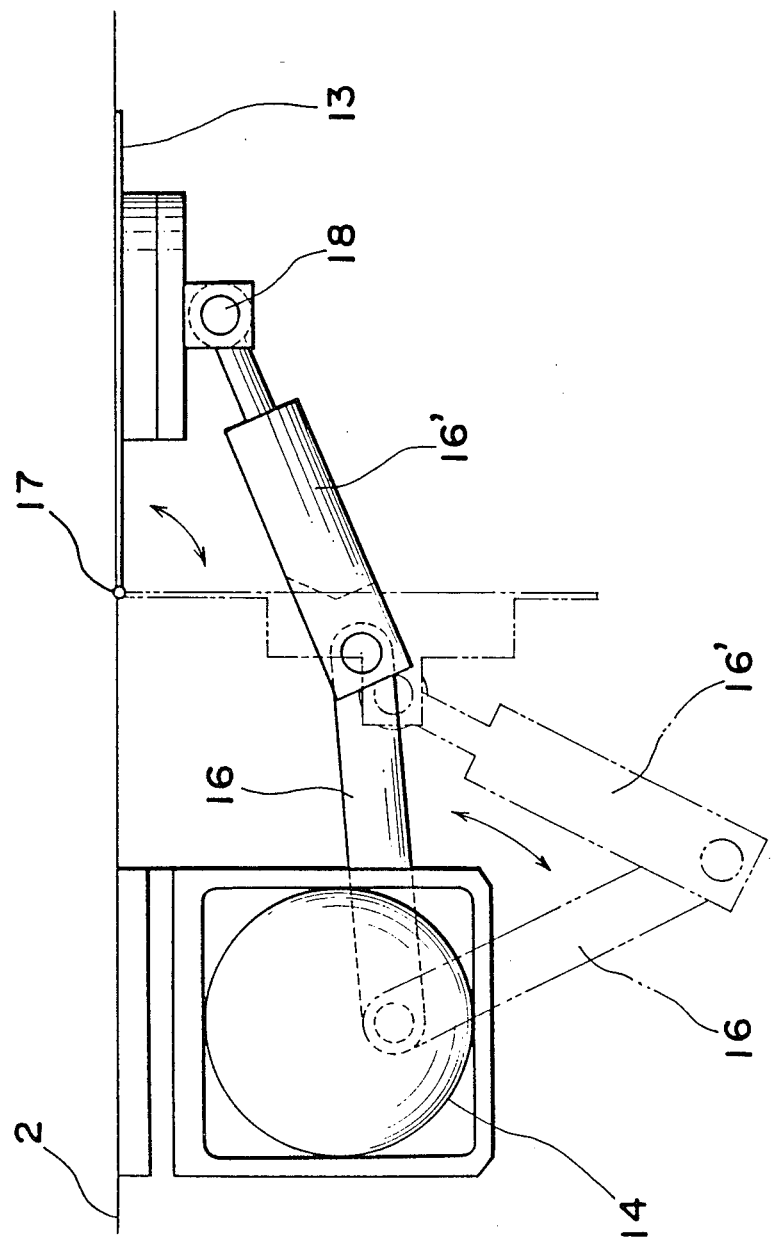
FIG. 5 is a top plan view indicative of operation of links employed in the incubator of FIG. 3.

Referring further to FIGS. 3 to 5, there is shown an incubator K2 according to a second embodiment of the present invention. In addition to the main door 2, the incubator K2 includes an auxiliary door 13 smaller in size than the main door 2. In this embodiment, the auxiliary door 13 is attached to the main door 2. In order to drive the auxiliary door 13, the incubator K2 includes a motor 14, a speed reduction unit 15, a first link 16, a second link 16' and a pair of hinges 17. The auxiliary door 13 is pivotally attached to the main door 2 by the hinges 17. Rotational speed of the motor 14 is reduced by the speed reduction unit 15 such that the first link 16 is actuated at the reduced rotational speed. The first and second links 16 and 16' are coupled with each other by a pin so as to constitute a turning pair. The other end of the second link 16' is coupled with a bar 18 mounted on the auxiliary door 13. The bar 18 axially extends in parallel with an axial direction of the hinges 17 which define a rotational axis of the auxiliary door 13.

Meanwhile, in this embodiment, although the auxiliary door 13 is attached to the main door 2 as shown in FIG. 3, it can also be so arranged that the auxiliary door 13 is attached to any one of other walls than the main cover 2.

FIG. 4 shows a construction of the second link 16'. The second link 16' includes a substantially rectangular arm holder 19, a T-shaped arm 20 supported by the arm holder 19 and a compression coiled spring 21 held in an opening formed in the arm holder 19. A base portion of the arm 20 is inserted into the opening of the arm holder 19 and a head portion of the arm 20 is mounted on the bar 18. Thus, the arm 20 is urged, at the base portion, by the coiled spring 21 towards the bar 18.

FIG. 5 shows opening and closing states of the auxiliary door 13., Output of the motor 14 is transmitted, through the speed reduction unit 15, to the first link 16 so as to rotate the first link 16 about an output shaft of the speed reduction unit 15. Since the first and second links 16 and 16' and the auxiliary door 13 constitute a three-joint link, the auxiliary door 13 is pivoted about the hinges 17 upon rotation of the first link 16 so as to be opened and closed.

Meanwhile, the second link 16' has the construction shown in FIG. 4. Thus, an urging force of the compression coiled spring 21 is transmitted to the auxiliary door 13 via the arm 20 so as to depress the auxiliary door 13 against the main door 2 at all times, so that air leakage from the auxiliary door 13 can be prevented. Furthermore, since the auxiliary door 13 for covering an opening smaller than that for the main door 2 may be opened and closed without the need for opening and closing the larger main door 2 each time the trays are taken out of and into the incubator housing 1, amount of high-humidity air leaking out of the incubator housing 1 is lessened, thereby resulting in reduction in change in atmosphere in the incubator housing 1. In addition, if such a need as maintenance operation in the incubator housing 1 arises, the larger main door 2 may be used and thus, working efficiency of the incubator K2 is not adversely affected.

Furthermore, in the incubator K2, if a seal made of elastic material such as rubber, etc. is bonded to a contact surface between the auxiliary door 13 and the main door 2, air leakage from the incubator housing 1 can be further effectively prevented.

As is seen from the foregoing description, in the incubator K2 of the present invention, since the auxiliary door is provided in addition to the main door and the auxiliary door is opened and closed by the door actuating mechanism employing the link mechanism incorporating the spring member, the auxiliary door can be smoothly brought into pressing contact with the incubator housing when the auxiliary door has been closed, thereby preventing air leakage from the incubator housing. Therefore, the incubator K2 can be effectively applied to a system for automatically taking the trays for cell culture out of and into a thermo-hygrostat such as an incubator.

Furthermore, since the auxiliary door can be restricted to a minimum size for taking the trays out of and into the incubator housing, change of atmosphere in the incubator housing can be lessened at the time of taking the trays out of and into the incubator housing.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. An incubator for cell culture comprising:
an incubator housing having a main door,
a tray stock disposed in said incubator housing for supporting a plurality of trays for cell culture,
a driving mechanism for rotating said tray stock,
said driving mechanism being provided outside said incubator housing and including a control means for stopping drive of said tray stock at a desired rotational position wherein said control means includes an encoder for detecting the rotational position of said tray stock,
an auxiliary door disposed on said incubator housing, and
a link mechanism including an arm coupled with said auxiliary door, a support member for supporting said arm and a compression coiled spring held by said support member such that said arm is urged toward said auxiliary door by said compression coiled spring, and a motor for driving said link mechanism, to open and close said auxiliary door perpendicularly to said main door.

* * * * *